United States Patent [19]

Gaillard et al.

[11] 4,001,343

[45] Jan. 4, 1977

[54] PROCESS FOR MANUFACTURING DICYCLOHEXANOL PROPANE BY HYDROGENATING DIPHENOL PROPANE

[75] Inventors: Jean Gaillard, Carrieres; Christian Lassau, Villepreux, both of France

[73] Assignee: Institut Francais du Petrole, Rueil-Malmaison, France

[22] Filed: May 9, 1975

[21] Appl. No.: 575,996

[30] Foreign Application Priority Data

May 10, 1974 France .............................. 74.16524

[52] U.S. Cl. .......................................... 260/631 H
[51] Int. Cl.² ...................................... C07C 29/20
[58] Field of Search ............................... 260/631 H

[56] References Cited
FOREIGN PATENTS OR APPLICATIONS 2,132,547    6/1971    Germany ............................ 260/631
7,035,300    11/1970   Japan ................................ 260/631

OTHER PUBLICATIONS

Kalina et al., Chem. Abst., vol. 58: 13846d (Czech. Pat. No. 103,572).
Murai et al., Chem. Abst., 70: 873025 (Japanese Pat. No. 6826859).
Terada, Bull. Chem. Soc. Jap., vol. 39, pp. 2194–2201 (1966).

Primary Examiner—Bernard Helfin
Assistant Examiner—James H. Reamer
Attorney, Agent, or Firm—Millen, Raptes & White

[57] ABSTRACT

Process for manufacturing dicyclohexanol propane by hydrogenating, with molecular hydrogen, in the presence of a hydrogenation catalyst, diphenol propane dissolved in 2 ethyl-hexanol, adding water at the end of the reaction, distilling the reaction product and separating from the distillate an aqueous phase and a 2 ethyl-hexanol phase, the latter being reused as solvent for the reaction.

10 Claims, No Drawings

PROCESS FOR MANUFACTURING DICYCLOHEXANOL PROPANE BY HYDROGENATING DIPHENOL PROPANE

This invention concerns an improvement to the manufacture of dicyclohexanol propane by hydrogenating diphenol propane, also named 4,4'-isopropylidene diphenol or bis phenol A, by means of molecular hydrogen.

Various methods for carrying out this hydrogenation are already known. The catalysts are usually noble metals or non-noble metals from group VIII, e.g., platinum, palladium, rhodium, nickel (nickel deposited on a carrier, Raney nickel, etc...) or cobalt. The proposed solvents were hydrocarbons, alcohols and ethers. The presence of water is usually favorable to the reaction. Among the alcohols used up to now, only a few ones gave satisfactory results. For example, according to the Japanese patent specification No. 4326859 (published on Nov. 19, 1968). the aliphatic alcohols have, as a general rule, an inhibiting effect on the hydrogenation: cyclohexanol is the only one which would lead to satisfactory hydrogenation rates.

The experimentation carried out by the applicants has shown, however, that cyclohexanol suffered from several disadvantages:

a. at the end of the reaction, cyclohexanol is removed by distillation and dicyclohexanol propane is recovered as distillation residue: the latter has a coloration which is assumed to result from the formation of peroxides during the distillation step, b. when using a homogeneous catalyst, it is not possible to directly reuse the distilled aqueous cyclohexanol which deactivates the catalyst, c. water in excess separates from cyclohexanol during the distillation as an aqueous phase easily separable from the cyclohexanol phase but which still contains, in solution, a substantial amount of cyclohexanol.

The lower aliphatic alcohols suffer from most of the above-mentioned disadvantages; moreover, their vapor pressure makes it necessary to proceed under high pressure in order to maintain a given partial hydrogen pressure.

According to the present invention, the solvent used for bisphenol is 2-ethyl-1-hexanol which has a unique series of properties and avoids all the above-mentioned disadvantages. Moreover, the viscosity of the solution, for the same content by weight of bis-phenol, is lower in the case of 2-ethyl-hexanol than in the case of cyclohexanol.

The bis-phenol hydrogenation reaction is well-known, for example from the U.S. Pat. No. 2 118 954 and it is not necessary to describe here the way to perform it.

The catalysts are usually metals or compounds of metals from group VIII of the periodic classification of elements, for example one of those mentioned above.

According to a preferred embodiment, there is used a homogeneous catalyst consisting of a mixture, or the reaction product, of a least one transition metal compound, for example, at least one compound of nickel, cobalt, iron, chromiun, zinc or molybdenum, with at least one metal hydride or one organometallic compound having at least one carbon-metal bond.

Catalysts of this type are described in particular in the French Patent No. 2 071 112 and in the French Patent application Ser. No. 73/16619 (corresponding to U.S. Patent application Ser. Nos. 91 190 of Nov. 19, 1970, now U.S. Pat. No. 3,904,692, and 467 900 of May 8, 1974).

The preferred organometallic compounds are of the formula $AlR_3$, in which the R groups, identical or different, are either hydrogen atoms, hydrocarbyl groups and/or hydrocarbyloxy groups. The ratio of the organoaluminum compound $AlR_3$ to the transition metal compound, expressed as the atomic ratio Al/transition metal, is for example from 0.1:1 to 20:1 and preferably, from 2:1 to 6:1.

When using a homogeneous catalyst, the total amount of the catalyst may be introduced at the beginning of the reaction or portion wise or continuously during the reaction.

According to a preferred embodiment, there is used a homogeneous catalyst formed of an organoaluminum compound, a nickel compound and an iron compound; at the end of the reaction, for example when the conversion rate reaches from 85 to 97%, an additional amount of nickel compound or of iron-free nickel-containing homogeneous catalyst, is added to the reaction medium.

The proportion of 2-ethyl-1-hexanol may vary within a wide range; for example, there may be used from 0.1 to 20 parts by weight of ethylhexanol per part by weight of bisphenol A.

The reaction temperature is usually from 120° to 220° C.

The hydrogen may be used in a pure state or diluted with inert gas.

The following examples illustrate the invention

EXAMPLE 1 (comparative)

The catalyst formed of 1.4 millimole of nickel octoate, 0.35 millimole of iron octoate and 5.6 millimole of triethylaluminum, is added to 100 g of bis-phenol A dissolved in 100 g of cyclohexanol. This operation is conducted at 180° C under a hydrogen pressure of 30 bars.

After 4 hours of reaction, no further hydrogen absorption is observed (the absorbed amount is substantially equal to the theoretical amount) and the temperature of the reactor is allowed to decrease down to 140° C. There is added 15 ml of water and the effluent is withdrawn. After separation of the catalyst, cyclohexanol is distilled and there is recovered a distillation residue containing 99 % of dicyclohexanol propane; said residue has a light yellow shade. The distillate separates in two phases: an upper phase consisting mainly of aqueous cyclohexanol and a lower phase consisting of water containing about 4 % by weight of cyclohexanol. This lower phase is discharged.

EXAMPLE 2 (comparative)

Example 1 is repeated, except that cyclohexanol is replaced by 100 g of the upper aqueous phase containing cyclohexanol, as obtained by distillation according to example 1. After 2 hours of reaction, the hydrogen absorption is stopped and it is observed that no more than 25 % of the theoretical amount of hydrogen has been absorbed.

EXAMPLE 3

Example 1 is repeated except that cyclohexanol is replaced by 100 g of 2-ethylhexanol.

The dicyclohexanol propane yield is unchanged and the product is substantially colorless; the lower aqueous phase, obtained by distillation of the reaction product, only contains 0.1 % by weight of 2-ethylhexanol. The alcohol loss is thus very low. The upper phase (ethylhexanol) contains less water than in example 1.

EXAMPLE 4

Example 3 is repeated, except that 2-ethylhexanol is replaced by the upper phase obtained by distillation of the reaction product of example 3.

The reaction progresses without difficulty, in the same manner as in example 3. The conversion of bisphenol A is substantially complete. No stopping of the hydrogen absorption is observed.

The same operation may be repeated several times.

We claim:

1. In a process for manufacturing dicyclohexanol propane by hydrogenating diphenol propane dissolved in a solvent, by molecular hydrogen in the presence of a hydrogenation catalyst selected from the group consisting of Raney nickel, nickel deposited on a carrier, a noble metal from group VIII, and a reaction product of at least one transition metal compound with $AlR_3$ wherein R is hydrogen, hydrocarbyl or hydrocarbyloxy, the improvement in which 2-ethylhexanol is used as the solvent.

2. A process according to claim 1, in which the catalyst is Raney nickel or nickel deposited on a carrier.

3. A process according to claim 1, in which the catalyst is a noble metal from group VIII.

4. A process according to claim 1, in which the catalyst results from the reaction of at least one transition metal compound with $AlR_3$ wherein R is hydrogen, hydrocarbyl or hydrocarbyloxy.

5. A process according to, in which, at the end of the reaction, water is added for deactivating the catalyst.

6. A process according to claim 1, in which the reaction product is fractionated by distillation and the distillate is separated into an aqueous phase and a 2-ethylhexanol phase which is reused as solvent for the reaction.

7. A process according to claim 1, in which 2-ethylhexanol is used in an amount from 0.1 to 20 parts by weight per part by weight of diphenol propane.

8. A process according to claim 1, wherein the catalyst is a reaction product of a compound of nickel, copper, cobalt, iron, zinc, chromium or molybdenum and $AlR_3$.

9. The process of claim 1, wherein said catalyst is formed from an organo-aluminum compound, a nickel compound and an iron compound.

10. The process of claim 9, wherein said catalyst is formed from nickel octoate, iron octoate, and triethylaluminum.

* * * * *

UNITED STATES PATENT AND TRADEMARK OFFICE
CERTIFICATE OF CORRECTION

PATENT NO. : 4,001,343
DATED : January 4, 1977
INVENTOR(S) : Jean Gaillard et al.

It is certified that error appears in the above—identified patent and that said Letters Patent are hereby corrected as shown below:

Column 4, line 7: After "to" insert -- Claim 1 -- .

Signed and Sealed this

Twenty-ninth Day of March 1977

[SEAL]

Attest:

RUTH C. MASON
*Attesting Officer*

C. MARSHALL DANN
*Commissioner of Patents and Trademarks*